US00PP21503P2

(12) United States Plant Patent
Heuger

(10) Patent No.: US PP21,503 P2
(45) Date of Patent: Nov. 16, 2010

(54) ***HELLEBORUS* PLANT NAMED 'HLR 120'**
(50) Latin Name: *Helleborus orientalis*
Varietal Denomination: HLR 120

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 12/459,840

(22) Filed: Jul. 8, 2009

(51) Int. Cl.
*A01H 5/00* (2006.01)

(52) U.S. Cl. ..... Plt./439
(58) Field of Classification Search ..... Plt./439

See application file for complete search history.

*Primary Examiner*—June Hwu
(74) *Attorney, Agent, or Firm*—C. A. Whealy

(57) ABSTRACT

A new and distinct cultivar of *Helleborus* plant named 'HLR 120', characterized by its upright plant habit; freely flowering habit; long flowering period; single greyed purple-colored flowers; and good garden performance.

2 Drawing Sheets

Botanical designation: *Helleborus orientalis.*
Cultivar denomination: 'HLR 120'.

BACKGROUND OF THE INVENTION

The present invention relates to a new and distinct cultivar of *Helleborus* plant, botanically known as *Helleborus orientalis*, and hereinafter referred to by the name 'HLR 120'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus orientalis*, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HLR 120'. These characteristics in combination distinguish 'HLR 120' as a new and distinct cultivar of *Helleborus:*

1. Upright plant habit.
2. Freely flowering habit.
3. Long flowering period.
4. Single greyed purple-colored flowers.
5. Good garden performance.

Compared to plants of the parent selections, plants of the new *Helleborus* are more uniform and more freely flowering.

Plants of the new *Helleborus* can be compared to plants of *Helleborus orientalis* 'HGC Merlin', disclosed in U.S. Plant Pat. No. 15,705. Plants of the new *Helleborus* differ primarily from plants of 'HGC Merlin' in the following characteristics:

1. Plants of the new *Helleborus* have larger flowers than plants of 'HGC Merlin'.
2. Flowers of plants of the new *Helleborus* are greyed purple in color whereas flowers of plants of 'HGC Merlin' are dark purple in color.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'HLR 120' grown in a container.

The photograph on the second sheet is a close-up view of a typical flower of 'HLR 120'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial Helleborus production. During the production of the plants, day temperatures ranged from 12° C. to 32° C. and night temperatures ranged from 3° C. to 18° C.

Plants were one year old when the photographs and the description were taken. In the following description, color references are made to The Royal Horticultural Society Colour Chart, 2007 Edition, except where general terms of ordinary dictionary significance are used.

Botanical classification: *Helleborus orientalis* 'HLR 120'.

Parentage:

*Female, or seed, parent.*—Unnamed proprietary seedling selection of *Helleborus orientalis*, not patented.

*Male, or pollen, parent.*—Unnamed proprietary seedling selection of *Helleborus orientalis*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright plant habit; moderately vigorous growth habit.

*Plant height.*—About 26.8 cm.

*Plant diameter* (*area of spread*).—About 31.1 cm.

Foliage description:

*Arrangement.*—Palmately compound with six leaflets per leaf.

*Leaf length.*—About 13.5 cm.

*Leaf width.*—About 14.6 cm.

*Leaflet length.*—About 10.3 cm.

*Leaflet width.*—About 3.1 cm.

*Leaf shape.*—Palmate; orbicular in outline.

*Leaflet shape.*—Obovate; lowest leaflets cleft to three-parted.

*Leaflet apex.*—Acute.

*Leaflet base.*—Attenuate.

*Leaflet margin.*—Sharply senate.

*Leaflet texture, upper and lower surfaces.*—Smooth, glabrous; leathery.

*Leaflet venation pattern.*—Pinnate.

*Leaflet color.*—Developing leaves, upper surface: Close to 144A. Developing leaves, lower surface: Close to 144A and 144B. Fully developed leaves, upper surface: Between N137A and 147A; venation, close to 144B to 144C. Fully developed leaves, lower surface: Close to 146B; venation, close to 144C.

*Petiole.*—Length: About 10 cm. Diameter: About 4 mm Texture, upper and lower surfaces: Smooth, glabrous. Color, upper and lower surfaces: Close to 144C to 144D.

Flower description:

*Flower shape and habit.*—Single rotate flowers; freely flowering habit, about six flowers developing per plant; petals not observed.

*Fragrance.*—None detected.

*Natural flowering season.*—Long flowering period; plants flower from January to March in Germany.

*Flower longevity on the plant.*—About ten days; flowers not persistent.

*Flower buds.*—Length: About 1.8 cm. Diameter: About 1.3 cm. Shape: Ovate. Color: Close to 187A.

*Flowers.*—Diameter: About 6.6 cm. Depth (height): About 2.6 cm.

*Sepals.*—Arrangement: About five in a single whorl. Length: About 4 cm. Width: About 2.9 cm. Shape: Broadly elliptic to obovate. Apex: Rounded. Margin: Entire, undulate. Texture, upper and lower surfaces: Smooth, glabrous; waxy. Color: When opening, upper surface: Close to 187B. When opening, lower surface: Close to N186D. Fully opened, upper surface: Between N186C and 187A. Fully opened, lower surface: Between N186C and 187B.

*Primary peduncles.*—Strength: Moderately strong. Length: About 21.1 cm. Diameter: About 6 mm. Aspect: Mostly upright, about 10° from vertical. Texture: Smooth, glabrous. Color: Close to 144B to 144C; towards the base, tinged with close to N186C.

*Reproductive organs.*—Stamens: Quantity per flower: About 60. Filament length: About 1.2 cm. Filament color: Close to 157C to 157D. Anther shape: Reniform. Anther length: About 1.5 mm. Anther color: Close to 150D. Pollen amount: Moderate. Pollen color: Close to 155A. Pistils: Quantity per flower: About four. Pistil length: About 1.2 cm. Stigma shape: Club-shaped. Stigma color: Close to 156D. Style length: About 1 cm. Style color: Close to 178A. Ovary color: Close to 144B. Nectaries: Quantity per flower: About 13. Length: About 8 mm. Diameter, apex: Close to 3.5 mm. Diameter, base: Close to 1 mm. Color: Close to 152C; towards the apex, close to 152A to 152B.

*Seeds/fruits.*—Seed and fruit development have not been observed.

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen/pest resistance: Plants of the new *Helleborus* have not been shown to be resistant to pathogens and pests common to *Helleborus*.

It is claimed::

1. A new and distinct *Helleborus* plant named 'HLR 120' as illustrated and described.

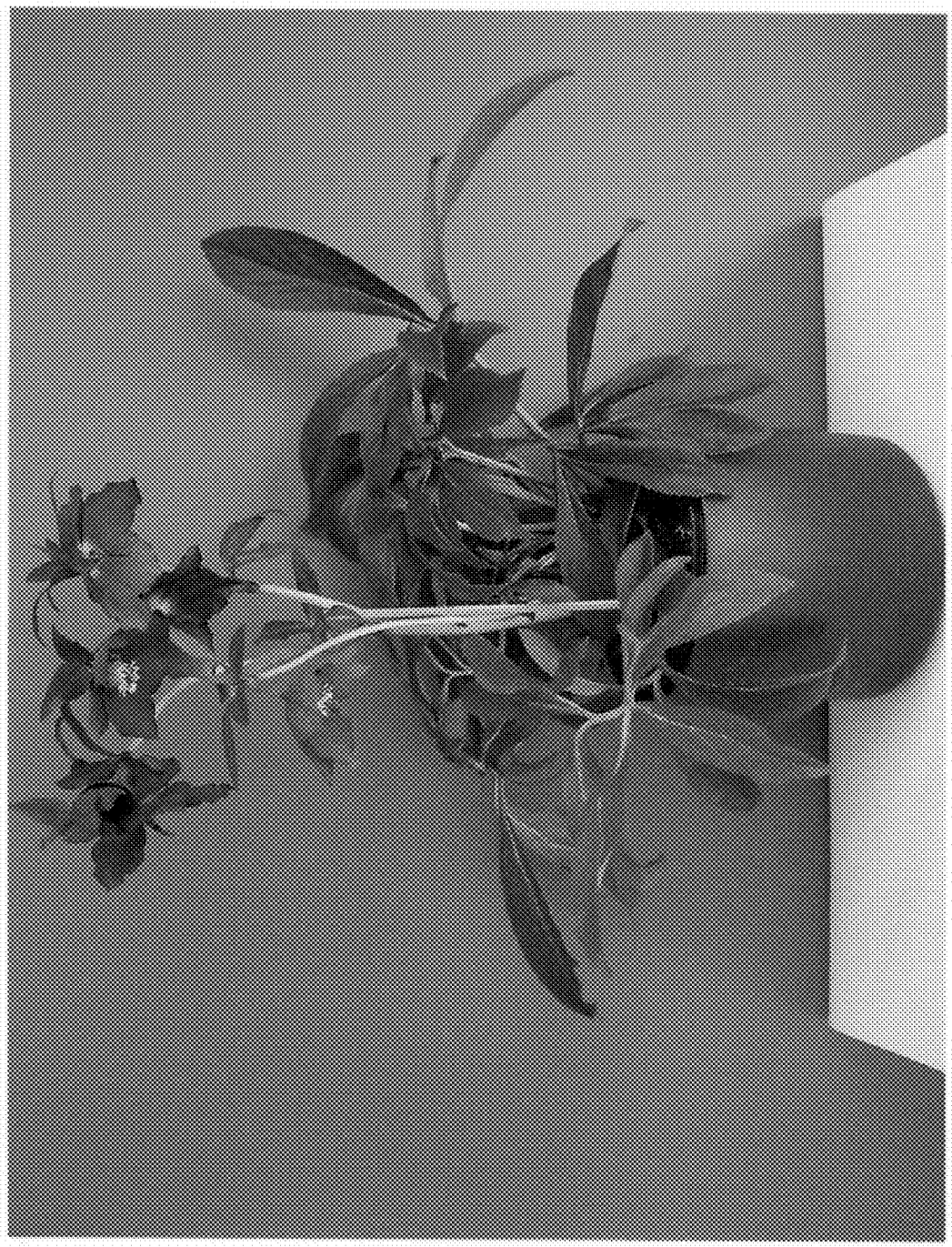

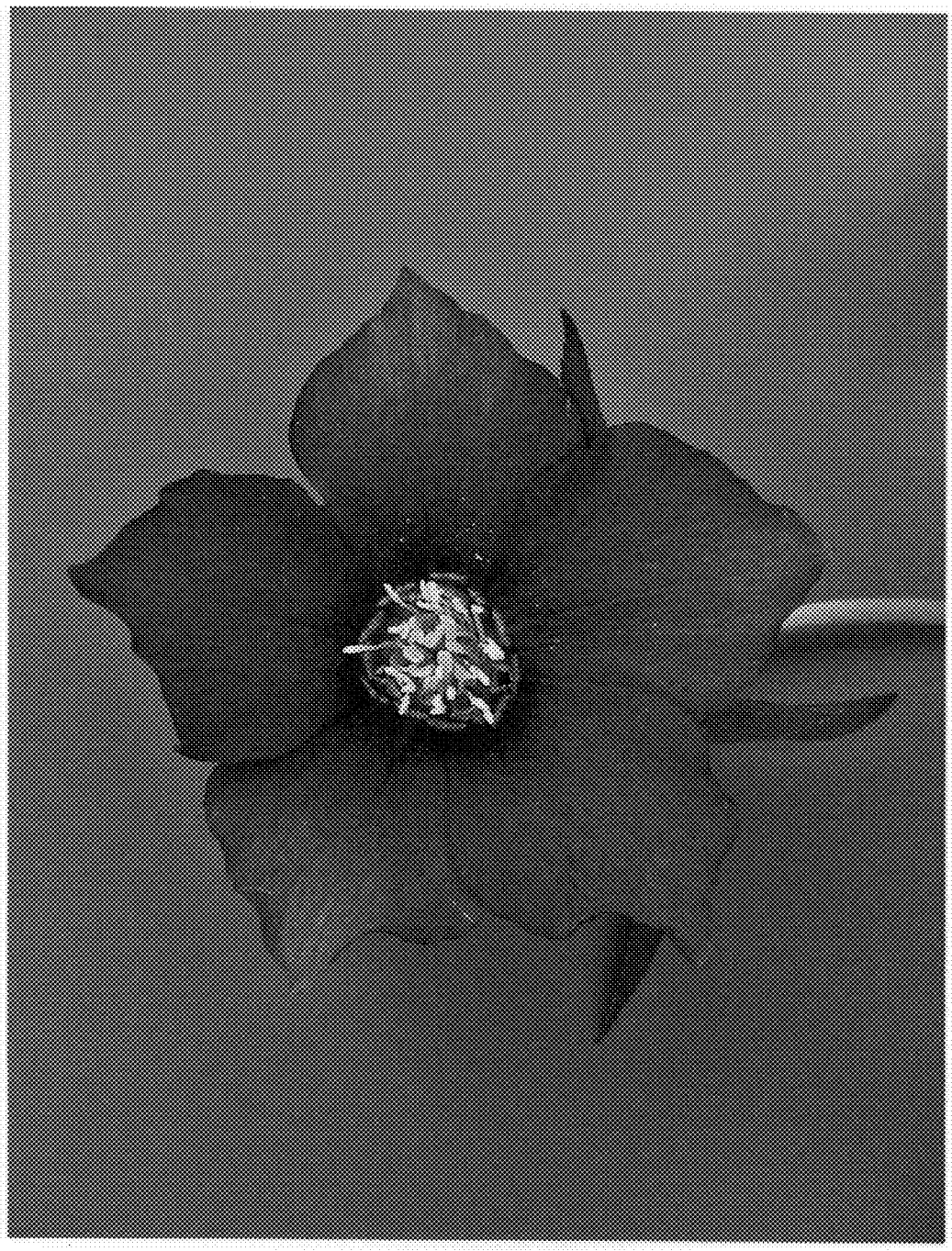

* * * * *